United States Patent
Stamm et al.

(10) Patent No.: US 10,631,943 B2
(45) Date of Patent: Apr. 28, 2020

(54) SURGICAL DRAPE

(71) Applicant: Medline Industries, Inc., Northfield, IL (US)

(72) Inventors: Alexis Stamm, Willowbrook, IL (US); Michael Seefeldt, Libertyville, IL (US); Mark Chua, Northbrook, IL (US)

(73) Assignee: Medline Industries, Inc., Northfield, IL (US)

( * ) Notice: Subject to any disclaimer, the term of this patent is extended or adjusted under 35 U.S.C. 154(b) by 380 days.

(21) Appl. No.: 15/678,407

(22) Filed: Aug. 16, 2017

(65) Prior Publication Data

US 2019/0053867 A1    Feb. 21, 2019

(51) Int. Cl.
*A61B 46/20* (2016.01)
*A61B 46/00* (2016.01)

(52) U.S. Cl.
CPC .............. *A61B 46/20* (2016.02); *A61B 46/00* (2016.02); *A61B 46/40* (2016.02); *A61B 2046/205* (2016.02)

(58) Field of Classification Search
CPC ......... A61B 46/20; A61B 46/00; A61B 46/40; A61B 2046/205; A61B 2046/201; A61B 46/17
See application file for complete search history.

(56) References Cited

U.S. PATENT DOCUMENTS

| | | | |
|---|---|---|---|
| 5,010,899 A | 4/1991 | Thompson | |
| 5,125,995 A | 6/1992 | D'Haese | |
| 5,383,476 A * | 1/1995 | Peimer | A61B 46/00 128/849 |
| 5,611,356 A | 3/1997 | Rothrum | |
| 5,991,923 A | 11/1999 | Maria | |
| 6,001,471 A | 12/1999 | Bries | |
| 6,216,700 B1 | 4/2001 | Griesbach | |
| 6,843,252 B2 | 1/2005 | Harrison | |
| 7,886,742 B2 | 2/2011 | Haines | |
| 8,011,371 B2 | 9/2011 | Rotolo | |
| 8,635,749 B2 | 1/2014 | Mayers | |
| 9,486,293 B2 | 11/2016 | McCollough | |
| 9,636,180 B2 | 5/2017 | Haines | |
| 9,668,822 B2 * | 6/2017 | Czajka, Jr. | A61B 46/00 |
| 2003/0121522 A1 * | 7/2003 | Gingles | A61B 46/00 128/853 |
| 2012/0222686 A1 | 9/2012 | Lockwood | |
| 2016/0008073 A1 | 1/2016 | Pecora | |
| 2017/0105807 A1 * | 4/2017 | Puentes | A61B 46/23 |

* cited by examiner

*Primary Examiner* — Tarla R Patel

(74) *Attorney, Agent, or Firm* — Fitch, Even, Tabin, & Flannery LLP

(57) ABSTRACT

Adjustable surgical drapes are provided for easily modifying the size of fenestrations in the drape to accommodate patients of different sizes.

14 Claims, 3 Drawing Sheets

SURGICAL DRAPE

FIELD

The present disclosure relates generally to surgical drapes and methods for making and using surgical drapes.

BACKGROUND

Surgical drapes are used to cover portions of a patient and surrounding areas to create a sterile barrier and maintain a sterile field during surgical procedures. Draping prevents the passage of fluids and microorganisms between nonsterile and sterile areas, and drapes may or may not include absorbent materials. Surgical draping may be used to maintain sterility in and about the surgical site not only during a medical procedure, but also after the operation is complete and the patient is recovering.

Surgical drapes may be used to cover a patient in a manner that exposes and isolates a prepared surgical site. Different types of drapes may be employed for different procedures, and may have features adapted for use on specific body parts or with specific instrumentation. In some cases, drapes are provided with a fenestration to allow a single drape to surround the surgical site on all sides. For some procedures, fenestrations of different sizes are used with patients of different sizes. In many cases, it has been necessary to stock plural drapes with fenestrations of different sizes.

It has now been found that a surgical drape can be prepared with an adjustable fenestration opening that readily permits changes to be made to the size of the fenestration through without cutting or tearing of the drape material. In some forms, a surgical drape comprises a large sheet of flexible material having a fenestration, the sheet having one or more areas of a first adhering material on at least one surface in order to attach a smaller removable panel having a smaller fenestration. The removable panel has one or more areas of a second adhering material complementary to the first adhering material in order to removably affix the panel to the sheet. Optionally, the drape may include removable strips to permit adjustments to the exterior dimensions of the drape. For instance, a drape may include overlapping strips affixed at one or more border areas that can be removed to decrease the length or width of the drape.

DETAILED DESCRIPTION

Figure 1:
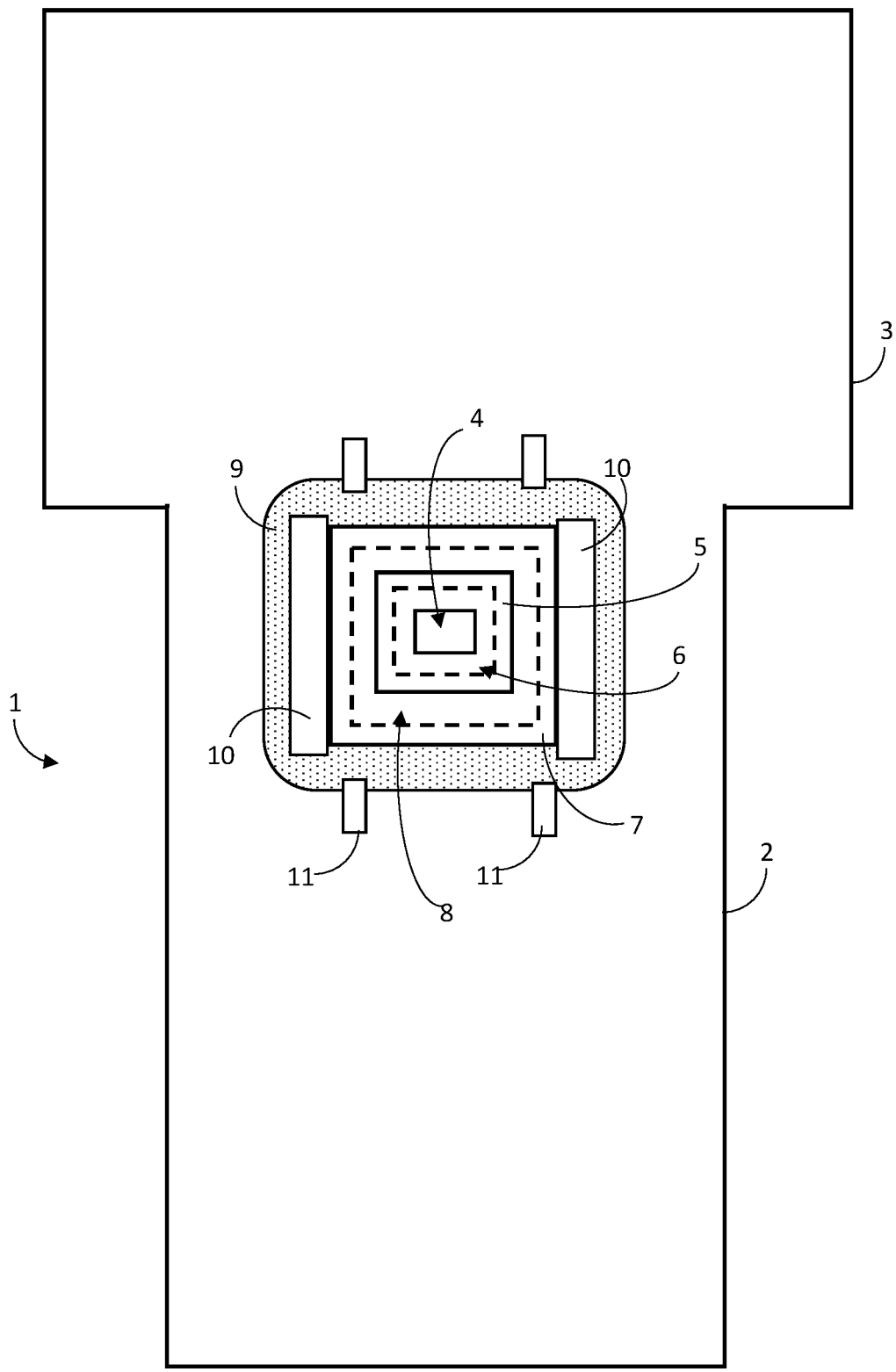
FIG. 1 is a plan view of an adjustable surgical drape according to one embodiment.

In various non-mutually exclusive embodiments, the present disclosure provides adjustable surgical drapes that readily permit changes to be made to the size of the fenestration through which a surgery is conducted without cutting or tearing of the drape material. In some forms, a surgical drape comprises a large sheet of flexible material having a fenestration, the sheet having one or more areas of a first adhering material on at least one surface in order to attach a smaller removable panel having a smaller fenestration. The removable panel has one or more areas of a second adhering material complementary to the first adhering material in order to removably affix the panel to the sheet. In some forms the adhering materials comprise complementary projections or grooves with a height of 1 mm or less, preferably 500 µm or less, and are substantially non-adherent to the flexible material of the sheet and/or panel. The areas of adhering material are configured to overlap when the panel is placed over the sheet with the fenestrations of the panel and sheet aligned. In some forms, the fenestrations of the panel and sheet may be substantially concentric when assembled. In this manner, the panel may be affixed to and removed from the sheet to increase or decrease the size of the fenestration in the drape without the adhering materials that affix the panel to the drape snagging the panel, drape, clothing, or other materials.

A second panel with an even smaller fenestration may be removably affixed to the first panel or the sheet in a similar fashion in order to provide three different fenestration sizes. Additional panels with different sizes and fenestrations may be provided to enhance the adjustability of the surgical drape. In some forms, the removable panels may have fenestrations of different shapes so that a surgeon or other individual in an operating room may adjust the shape of the fenestration without selecting an entirely different surgical drape.

An adjustable surgical drape may thus be provided for positioning over a patient and removing one or more panels to select an appropriately sized fenestration for a given procedure. The surgical drape may be provided as a packaged plurality of assembled sheets of a first material having different sizes, each sheet comprising a fenestration, the sheets stacked and joined from largest to smallest so that the fenestrations are substantially concentric. Each sheet may be removably affixed to at least one adjacent sheet at least in part by opposed complementary adhering materials each comprising projections or grooves with a height of about 500 µm or less. The drape may be provided in sterile packaging for use in an operating room. The panel or panels may be removed from the drape prior to or after positioning the drape over the patient to provide a fenestration of a desired size. In some embodiments, the surgical drape may have an adhesive material applied to a patient-facing surface to permit the drape to be fixed in place on the patient's skin. The drape optionally may include an incise film layer.

In some forms, surgical drapes as described herein are made from materials selected to create and maintain an effective barrier that minimizes the passage of microorganisms between sterile and non-sterile areas. In some forms, the drape material is resistant to blood, aqueous fluid, and abrasion, and is also relatively lint free. In some embodiments, the drape materials are selected to reduce risk of static charges on the drape. The materials of the drape may also be penetrable by steam or gas to permit sterilization. One preferred material for the main body of the surgical drape is a spunbond-meltblown-spunbond (SMS) material in which a layer of meltblown material is sandwiched between two layers of spunbond materials.

In some forms, the adhering material that affixes the panels to one another or to the largest flexible sheet is a non-tack adhesive or adhering material. In some forms, the adhering material comprises a plurality of tiny, tapered projections and/or grooves that engage one another to provide sufficient binding force to hold thin sheets of draping material together. The projections/grooves of the adhering material of one panel or sheet are complementary to the projections/grooves of the adhering material of the adjacent panel/sheet so that the materials interlock and adhere to one another, but advantageously do not adhere to inert materials. As a result, the adhering materials are preferably not sticky to the touch and do not adhere to any significant degree to surgical scrubs, gloves, or most draping materials, but bond strongly with a complementary adhering material.

In some forms, the adhering materials comprise a first adhering element comprising a flexible material having a surface that includes a first array of tapered protrusions thereon and a second adhering element having a surface that includes a second array of tapered protrusions or tapered grooves. In some forms, the adhering materials are elastomeric. In some embodiments, the arrays of tapered protrusions or tapered grooves of the first and second adhering materials have a periodicity that is substantially complementary. Thus, contacting the first adhering element with the second adhering element results in a substantial interleaving of the tapered protrusions of the first array with the tapered protrusions or tapered grooves of the second array. In some forms, this interleaving may provide a reversible adhering interaction having a force per unit area of about 1 Newton/$cm^2$ to about 100 $N/cm^2$ between the first and second adhesive elements. However, if either of the first or second adhesive elements is contacted with an inert surface or surface without substantially complementary arrays of tapers or grooves, an interaction having a force per unit area that is less than 50% of the adhesive interaction with a substantially complementary adhering element results. The adhering interaction between the first and second adhering elements may be reversible.

In particular forms, the protrusions or grooves of the first and second adhering elements may have a vertical dimension (from a base of the protrusion to the tip of the tapered portion) of about 1 µm to about 500 µm, and the bases of the tapers may have a lateral dimension of about 1 µm to about 100 µm. In some forms, the tapered body portions may have a tapered sidewall with an average angle of taper of about 5° to about 50°. In some forms, the tip portions of the elements have a maximum lateral dimension at the point where the tip portion meets the tapered body portion, which in some forms may have a lateral dimension of about 50 nm to about 50 µm. The tips of the tapered elements may be blunt or pointed. In some embodiments, the lateral dimensions of the tip portions and base portions of the protrusions or grooves have a dimensional ratio of about 1:2 to about 1:2,000. The tapered elements in some forms do not contact other elements of the same array, and may in some forms have a surface roughness of about one order of magnitude or less that the lateral dimensions of the elements. The tapered elements of an array may include functional groups capable of interacting with functional groups of a complementary array, for instance by non-covalent interactions, covalent bonding, or combinations thereof. In some forms, tip portions of the elements may include a liquidphobic group. In some forms, the tapered elements are substantially free of barbs, hooks, spirals, loops, seta, spatula, suction cups, or other external structural elements. Examples of adhering materials for use in affixing portions of the described surgical drapes are described in U.S. Pat. No. 8,635,749, which is hereby incorporated in its entirety as if set forth herein.

Materials making up the arrays of tapered protrusions and or grooves may be, for example, polymeric materials that are able or flex and undergo deformation (i.e., compression, torsional flexing, extension, and the like) in response to an external force. In some embodiments, the materials include elastomeric materials (i.e., those that elastically deform and then recover completely, or almost completely, to their original shape/dimensions, after the application of an applied load) or plastically deformable materials (i.e., those that deform permanently, or semi-permanently, following the application and release of an applied load). Examples of flexible materials for use in adhering elements include, but are not limited to, flexible glasses, flexible metals, various polymers, such as poly(dialkylsiloxanes) (e.g., poly(dimethylsiloxane) (PDMS)), poly(silsesquioxane), polyisoprene, polybutadiene, poly(styrene), poly(acrylamide), poly(butylstyrene), poly(propylene) (PP), poly(ethylene), poly(styrene)-poly(propylene) copolymers, poly(styrene isoprene styrene) copolymers (PSIS), styrene butadiene copolymers (SBC), polychloroprene, acryloxy elastomers, fluorinated and perfluorinated elastomers (e.g., TEFLON®, E. I. DuPont de Nemours & Co., Wilmington, Del.), copolymers thereof, and combinations thereof. Other materials suitable for use as the adhesive elements include those materials disclosed in U.S. Pat. Nos. 5,512,131; 5,900,160; 6,180,239; and 6,776,094, all of which are incorporated herein by reference in their entirety. In some embodiments, the composition of the elastomeric material is substantially homogeneous, though in others, the composition of the elastomeric material has a gradient, or a multi-laminate structure.

Additional materials that can be used as the flexible materials of the adhesive elements include, but are not limited to, saturated elastomers such as ethylene propylene rubber, epichlorohydrin rubber, polyacrylic rubber, silicone rubbers, butadiene rubbers, fluorosilicone rubber, fluoroelastomers, such as VITON®. and TECNOFLON®, perfluoroelastomers, tetrafluoro ethylene/propylene rubbers, chlorosulfonated polyethylene, and ethylene vinyl acetate. In further embodiments, unsaturated elastomers such as thermoplastic elastomers, polyurethane, resilin, elastin, polyimides and phenol formaldehyde polymers, can be used in the practice of the present invention.

In some embodiments, the tapered protrusions of the first adhesive element and the tapered protrusions or tapered grooves of the second adhesive element are substantially free from barbs, hooks, spirals, loops, seta, spatulae, suction cups, or any other external structural elements. In some forms, contacting the first and second adhesive elements results in contact of greater than 30% of the total surface area that is desired to be contacted between the first array and the second array. In further embodiments, the adhesive systems comprise one or more liquids (e.g., water, lubricants, fouling agents, blood, surfactants, etc., and mixtures thereof) present between the first and second arrays. In some forms, the adhered system is substantially impermeable to liquid.

In some forms, complementary adhering elements may be electrostatically complementary. Electrostatically complementary adhesive elements are generated when the two elements are selected from opposite ends of the triboelectric series. Triboelectric materials exhibit the triboelectric effect—a type of contact electrification in which certain materials become electrically charged after they come into contact with another different material and are then separated (such as through rubbing), thereby generating an electrostatic attraction between the materials. The polarity and strength of the charges produced differ according to the materials, surface roughness, temperature, strain, and other properties. Exemplary materials include dielectrics, ceramics, and polymers. For example, the first adhesive element can comprise nylon and the second adhesive element can comprise TEFLON®. Additional materials include ionomers that can be chemically tailored, to provide bound ionic functionality to control the sign of the charge. Adhering elements can be directly prepared from triboelectric materials (e.g., molded, formed or otherwise generated from the materials), or the adhering elements can be coated with the triboelectric materials (e.g., via spray coating, painting, dip-coating, etc.). The triboelectric effect thus adds further adhering force in addition to that generated between the tapered protrusions and/or grooves. The adhering elements can also be prepared in patterns such that opposing sides of the adhesive elements (i.e., the elements that will adhere to one another) are patterned with electrostatically complementary materials.

In some forms, adhering elements of different arrays may be magnetically complementary. Magnetically complementary adhering elements are those which are attracted to each other via a magnetic force, and may be prepared from magnetically complementary materials, for example, from a dispersion of magnetic nanoparticles or microparticle platelets. The magnetic particles can be properly aligned prior to polymerization into final adhesive elements. In some forms, adhering elements can be coated with magnetic materials, or can be magnetized via contact magnetization using a stamp that is patterned in the geometry of the desired magnetic field. The adhering elements can be prepared in patterns such that opposing sides of the adhering elements (i.e., the elements that will adhere to one another) are patterned with magnetically complementary materials.

FIG. 1 illustrates one form of adjustable surgical drape 1 having a main body 2 and an optional anesthesia screen section 3. The drape is made from a flexible material, preferably a thin plastic such as polypropylene. Preferably the drape comprises spunbond-meltblown-spunbond (SMS) polypropylene. The drape material may have antimicrobial characteristics, or may be coated or impregnated with antimicrobial materials to prevent migration of bacteria during surgical procedures. A separate layer of antimicrobial film may alternatively be employed to reduce risk of infection. As presented, the drape includes a relatively small fenestration 4 or window through which a surgeon may interact with an incision in a patient covered by the drape. If a larger exposed area of the patient is desired or necessary, the surgeon may peel away the top panel 5 to reveal an underlying medium fenestration 6 intermediate in size between the small fenestration 4 and top panel 5. Preferably the top panel 5 is affixed to the underlying lower panel 7 that includes medium fenestration 6 using complementary arrays of tapered nanoscale or microscale elements so that the nano- or micro-scale elements do not substantially adhere to unwanted surfaces once the top panel 5 is removed. If a large fenestration is necessary, lower panel 7 may be peeled away to reveal a large fenestration 8. The lower panel 7 is preferably affixed to the drape body 2 using complementary arrays of nano- or micro-scale tapered elements on each article. Additional removable panels may be provided so that additional fenestration size options are available or to close fenestrations prior to or after use.

The various fenestrations in different removable panels allow a single drape to be used in multiple types of surgical procedures and with various types of patients. For instance, the small fenestration may be about 7 inches by 7 inches, the medium fenestration may be about 12 inches by 12 inches, and the large fenestration may be about 18 inches by 18 inches to allow the adjustable surgical drape to be used with patients of all sizes, from pediatric to bariatric, instead of requiring three or more different drapes.

The surgical drape may also be provided with various additional features. For instance, a layer of absorbent material 9 may be incorporated, for instance on the top (surgeon-facing) surface of the drape. Any conventional absorbent material may be used, such as reinforced poly. Absorbent materials may also be incorporated into one or more panels. Troughs or fluid collection pouches 10, generally made of clear plastic film, may be positioned near the fenestrations and absorbent layer in order to prevent spillage of blood and other matter form the surgical site. One or more tube or line holders 11, preferably constructed of hook-and-loop fasteners, may be provided to hold instruments in place. Other conventional features for drapes used in specific procedures may also be incorporated into the adjustable drape.

Figure 2:
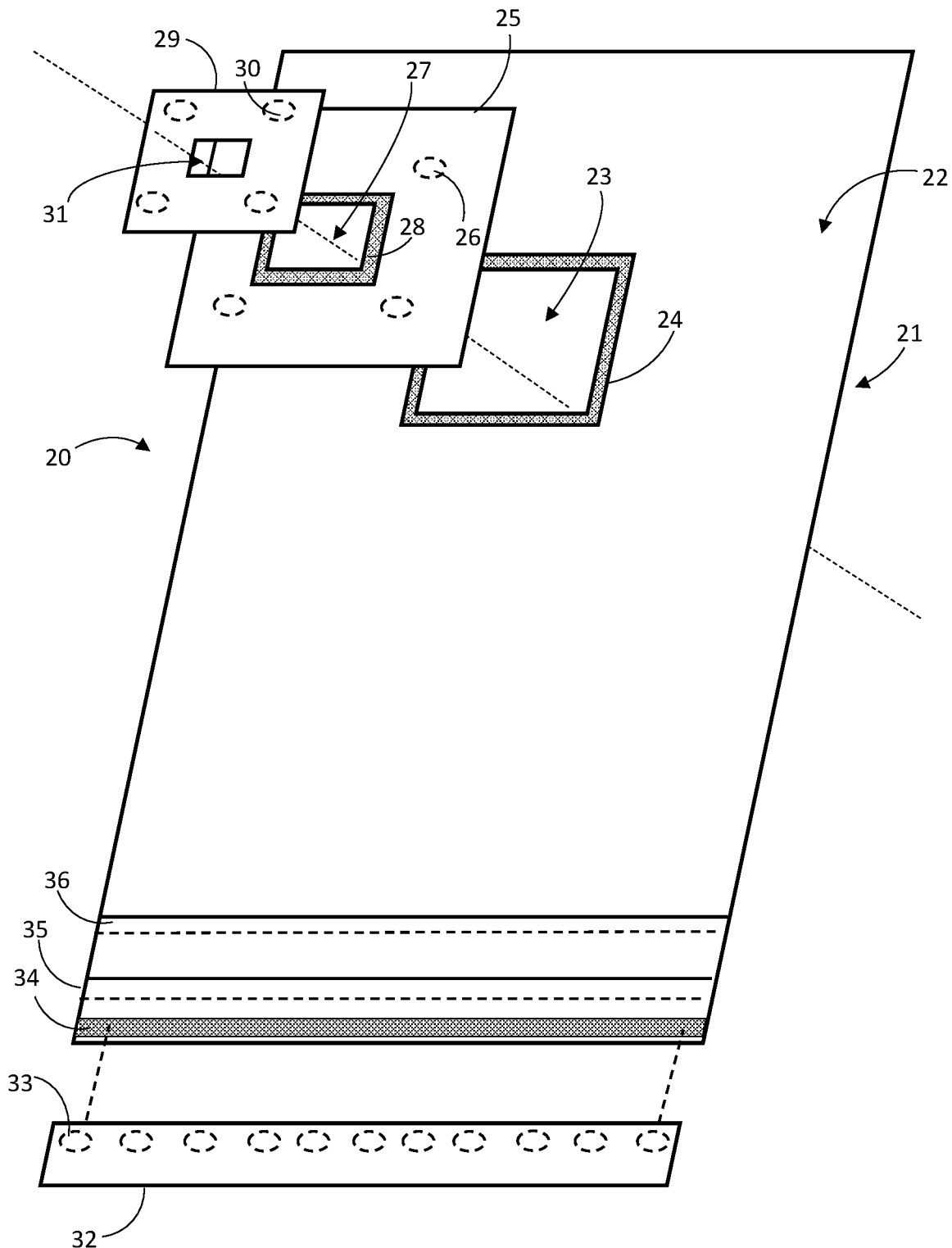
FIG. 2 is an exploded view of another embodiment of the adjustable surgical drape.

FIG. 2 shows another form of surgical drape 20, this time in a perspective exploded view in order to demonstrate removability of the panels. The drape 20 has a lower (patient-facing) surface 21 and upper (surgeon-facing) surface 22. A first fenestration 23 is provided in the drape, and one or more areas of a first adhering material 24 are provided near the fenestration 23. As shown, the first adhering material 24 substantially surrounds the first fenestration 23, but other configurations are possible and the adhering material may be provided in a plurality of discrete areas. A first panel 25 may be removably affixed to the drape by contacting areas of a second adhering material 26 to the first adhering material. The first panel 25 is larger than the first fenestration 23 in order to completely cover the fenestration when in place. Areas of second adhering material 26 are shown in broken lines to indicate that they are placed on the underlying surface of the panel 25. The first and second adhering materials are complementary to adhere to one another, and are preferably comprised of arrays of nano- or micro-projections that do not adhere to the material of the drape 20 or panel 25 or other inert materials. Although discrete areas of the second adhering material 26 are shown, it is contemplated that a ring or continuous strip of material may be provided on the rear surface of the first panel 25 in order form a seal with the continuous area of first adhering material 24 below. Regardless of the configuration of adhering materials, areas of first and second adhering materials should be positioned and aligned to allow the first panel 25 to be securely fixed to the drape 20. The first panel is provided with a fenestration 27, and is provided with a third adhering material 28 on its upper surface, opposite the second adhering material 26, to secure a second panel 29 having areas of a fourth adhering material 30. The second panel 29 includes a third fenestration 31, and may optionally include an additional adhering material on its upper surface to receive one or more additional panels.

To adjust the exterior dimensions of the drape 20, one or more edges may be formed with one or more strips to be peeled away as needed. At the bottom of FIG. 2 a removed edge strip 32 is shown and may be reattached via adhering elements 33 to an adhering area 44 of the drape. The area to which the removed strip 32 attaches may itself be a removable strip 35, and may attach to yet another removable strip 36 in order to provide increased adjustability to the overall size of the surgical drape. The number of adjustable edge portions may be greater or fewer than shown, and may be eliminated altogether. Adjustable edge portions may also have different shapes, and may comprise removable frames that border more than one side and simultaneously alter the dimensions of the drape in more than one direction when removed or added. Use of non-stick adhering nano- or micro-scale materials, as used to attach the above-described panels 25 and 29 to the drape, prevents the drape from clinging to unwanted objects or surfaces even when one or more edge portions have been removed. It is also possible to provide these portions as perforated tear-away strips.

Figure 3:
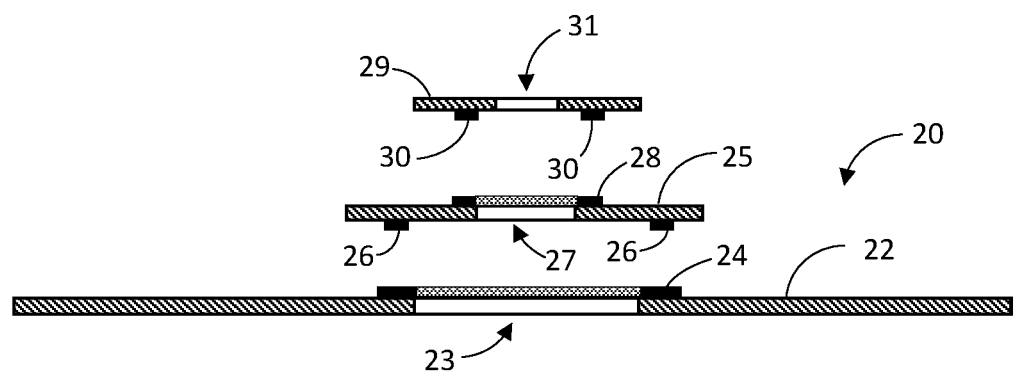
FIG. 3 is a cross-sectional view of the drape of FIG. 2.

A cross-section of drape 20 from FIG. 2 through the fenestrations of the drape is shown in FIG. 3, illustrating the upper surface 22 of the drape and first adhering material 24 complementary to a second adhering material 26 on a lower surface of the first removable panel 25. As discussed above, the upper surface of panel 25 includes a third adhering material 28 complementary to a fourth adhering material 30 on the bottom surface of the second panel for affixing the second panel 29 to the first panel 25. When assembled, the drape will initially have a small fenestration 31, but removal of the second panel 29 reveals a medium fenestration 27 and removal of both panels reveals a large fenestration 23.

Figure 4:
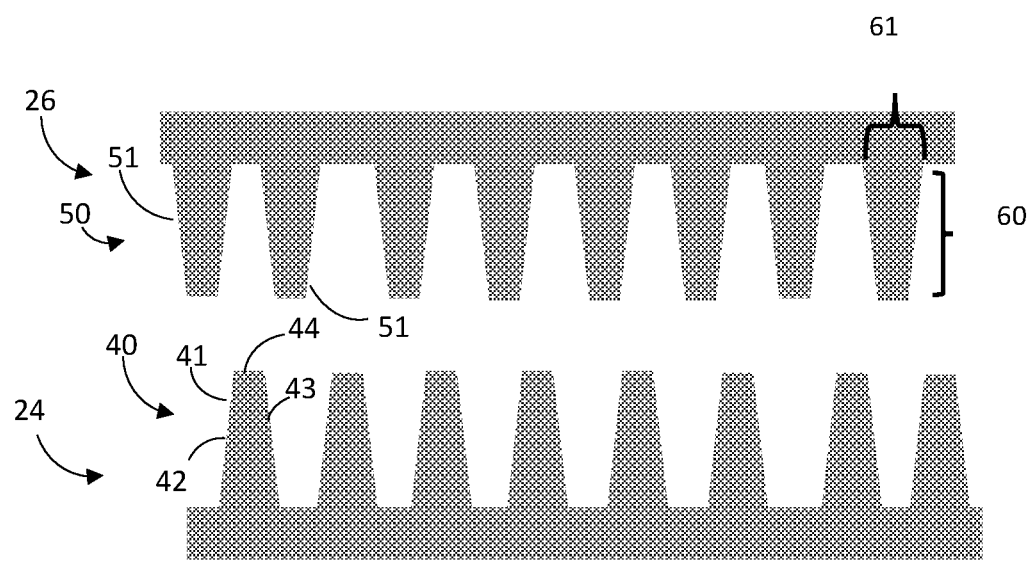
FIG. 4 is a greatly enlarged view of one form of adhering material for use in the invention.

With reference now to FIG. 4, the first adhering element 24 comprises an array 40 of elongate nano- or micro-projections 41 each having converging side surfaces 42 and 43. The angle of side surfaces may be changed as desired. The tips 44 of the projections may be blunt as shown or pointed. The projections 41 have a size and periodicity permitting them to interlock with an array 50 of nano- or micro-projections 51 from the second adhering material 26. The tapered projections may have any vertical dimension, shown as 61 in FIG. 4, but preferably extend from the surface of the adhesive element about 500 nm to about 1 mm, preferably about 1 μm to about 500 μm, or about 100 μm to about 300 μm, about 150 μm to about 200 μm. The lateral width of the base of the tapered portion, shown as 62, may be about 500 nm to about 500 μm, or about 1 μm to about 300 μm, or about 1 μm to about 250 μm, or about 1 μm to about 150 μm, or about 1 μm to about 100 μm, or about 1 μm to about 50 μm.

It is therefore seen that a surgical drape having an adjustable fenestration may be provided.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

The invention claimed is:

1. A surgical drape comprising:
   a sheet comprising a flexible material and having a first sheet fenestration and one or more areas of a first adhering material, the first adhering material comprising projections or grooves with a height of 500 μm or less;
   a removable first panel overlapping the first fenestration, the first panel including a first panel fenestration that is smaller than said first sheet fenestration, the removable first panel further having one or more areas of a second adhering material comprising projections or grooves with a height of 500 μm or less, the second adhering material being complementary to the first adhering material and capable of adhering thereto, the first and second adhering materials being substantially non-adherent to said flexible material;
   the areas of the second adhering material configured to overlap the areas of the first adhering material to thereby removably affix said first panel to said sheet;
   said first panel comprising one or more areas of a third adhering material on a side of the first panel opposite the second adhering material, said third adhering material comprising projections or grooves with a height of 500 μm or less, and
   a removable second panel overlapping the first panel fenestration, the removable second panel having a second panel fenestration that is smaller than said first patent fenestration, the second panel comprising one or more areas of a fourth adhering material comprising projections or grooves with a height of 500 μm
   the fourth adhering material being complementary to the third adhering material and capable of adhering thereto, the third and fourth adhering materials being substantially non-adherent to said flexible material
   the areas of the fourth adhering material configured to overlap the one or more areas of third adhering material to affix the second panel to the first panel.

2. The surgical drape of claim 1, wherein the first and second adhering materials are elastomeric.

3. The surgical drape of claim 1, wherein the protrusions or grooves of the first and second adhering materials have a height of about 1 μm to about 500 μm.

4. The surgical drape of claim 1, wherein the protrusions or grooves of the first and second adhering materials are substantially free from barbs, hooks, spirals, or loops.

5. The surgical drape of claim 1, comprising at least one fluid-collection pouch.

6. The surgical drape of claim 1, wherein the projections of the adhering materials have an average angle of taper of about 5° to about 50°.

7. The surgical drape of claim 1, wherein the flexible material is a spunbond-meltblown-spunbond material in which a layer of meltblown material is sandwiched between two layers of spunbond materials.

8. The surgical drape of claim 1, wherein the first and second adhering materials are elastomeric.

9. The surgical drape of claim 1, wherein the protrusions or grooves of the first and second adhering materials have a height of about 1 μm to about 500 μm.

10. The surgical drape of claim 1, wherein the protrusions or grooves of the first and second adhering materials are substantially free from barbs, hooks, spirals, or loops.

11. The surgical drape of claim 1, comprising at least one fluid-collection pouch.

12. The surgical drape of claim 1, wherein the projections of the adhering materials have an average angle of taper of about 5° to about 50°.

13. The surgical drape of claim 1, wherein the flexible material is a spunbond-meltblown-spunbond material in which a layer of meltblown material is sandwiched between two layers of spunbond materials.

14. A method comprising:
   providing the drape of claim 1, and
   in either order appropriate
      positioning said drape over a patient, and
      removing said first panel.

\* \* \* \* \*